United States Patent
Portney et al.

(10) Patent No.: US 10,181,013 B2
(45) Date of Patent: Jan. 15, 2019

(54) CARTRIDGE-BASED MEDICATION DISPENSING

(71) Applicants: Nathaniel G. Portney, San Diego, CA (US); Valdemar Portney, Newport Coast, CA (US)

(72) Inventors: Nathaniel G. Portney, San Diego, CA (US); Valdemar Portney, Newport Coast, CA (US)

(*) Notice: Subject to any disclaimer, the term of this patent is extended or adjusted under 35 U.S.C. 154(b) by 509 days.

(21) Appl. No.: 14/526,513

(22) Filed: Oct. 29, 2014

(65) Prior Publication Data

US 2015/0051730 A1 Feb. 19, 2015

Related U.S. Application Data

(63) Continuation-in-part of application No. 13/204,407, filed on Aug. 5, 2011.

(60) Provisional application No. 61/897,087, filed on Oct. 29, 2013, provisional application No. 62/066,801, filed on Oct. 21, 2014.

(51) Int. Cl.
*G06F 19/00* (2018.01)
*H04W 4/00* (2018.01)
*H04W 4/70* (2018.01)

(52) U.S. Cl.
CPC .......... *G06F 19/3462* (2013.01); *G06F 19/00* (2013.01); *H04W 4/70* (2018.02); *A61M 2205/35* (2013.01); *A61M 2205/3569* (2013.01)

(58) Field of Classification Search
CPC .......... G06F 19/3462; A61M 2205/35; A61M 2205/3569
USPC .................................. 700/231–244
See application file for complete search history.

(56) References Cited

U.S. PATENT DOCUMENTS

| | | | | |
|---|---|---|---|---|
| 8,397,946 | B2* | 3/2013 | Portney | B65D 83/0454 221/113 |
| 8,600,548 | B2* | 12/2013 | Bossi | G06F 19/3462 700/240 |
| 8,670,865 | B2* | 3/2014 | Coe | A61J 7/0481 700/232 |
| 9,566,395 | B2* | 2/2017 | Denny | B65D 83/02 |
| 2006/0058724 | A1* | 3/2006 | Handfield | A61J 7/0084 604/20 |
| 2008/0035520 | A1* | 2/2008 | Caracciolo | G06F 19/3462 206/531 |

(Continued)

*Primary Examiner* — Michael Collins
(74) *Attorney, Agent, or Firm* — Hackler Daghighian Martino & Novak

(57) ABSTRACT

A pill dispensing system includes an electronic mobile communication device with a wireless transmitter and receiver. A pill cartridge has a cartridge body storing a plurality of pills, where the cartridge body includes an electronic tag storing data. A pill cartridge dispenser is configured to receive at least one of the pill cartridge and configured to electromechanically control dispensing of the plurality of pills from the cartridge body, where the pill cartridge dispenser is configured to be in wireless communication with the electronic mobile communication device. The electronic mobile communication device is configured to wirelessly read the data stored on the electronic tag or wherein the pill cartridge dispenser is configured to wirelessly read the data stored on the electronic tag. The electronic mobile communication device wirelessly communicates with the pill cartridge dispenser to dispense at least one pill from the plurality of pills within the pill cartridge.

17 Claims, 8 Drawing Sheets

(56) References Cited

U.S. PATENT DOCUMENTS

| | | | | |
|---|---|---|---|---|
| 2009/0281657 A1* | 11/2009 | Gak | ............... | A61J 7/0481 |
| | | | | 700/242 |
| 2010/0312383 A1* | 12/2010 | Naik | ............... | A61J 7/0076 |
| | | | | 700/242 |
| 2014/0155827 A1* | 6/2014 | Ostrander | ............. | B65D 83/02 |
| | | | | 604/111 |
| 2015/0251839 A1* | 9/2015 | Denny | ............... | B65D 83/02 |
| | | | | 340/686.6 |

* cited by examiner

Graphical definitions of elements and transfers in Cartridge-based medication dispensing tree

[P] = pill

☐ = tag

Ⓒ = prefilled cartridge with programmed tag

—·—·→ = pill transfer

⟶ = cartridge transfer and tag transfer

⇕ = data input and two-way data transfer

⇅ = two-way data transfer

- - -→ = one-way data transfer

FIG. 1

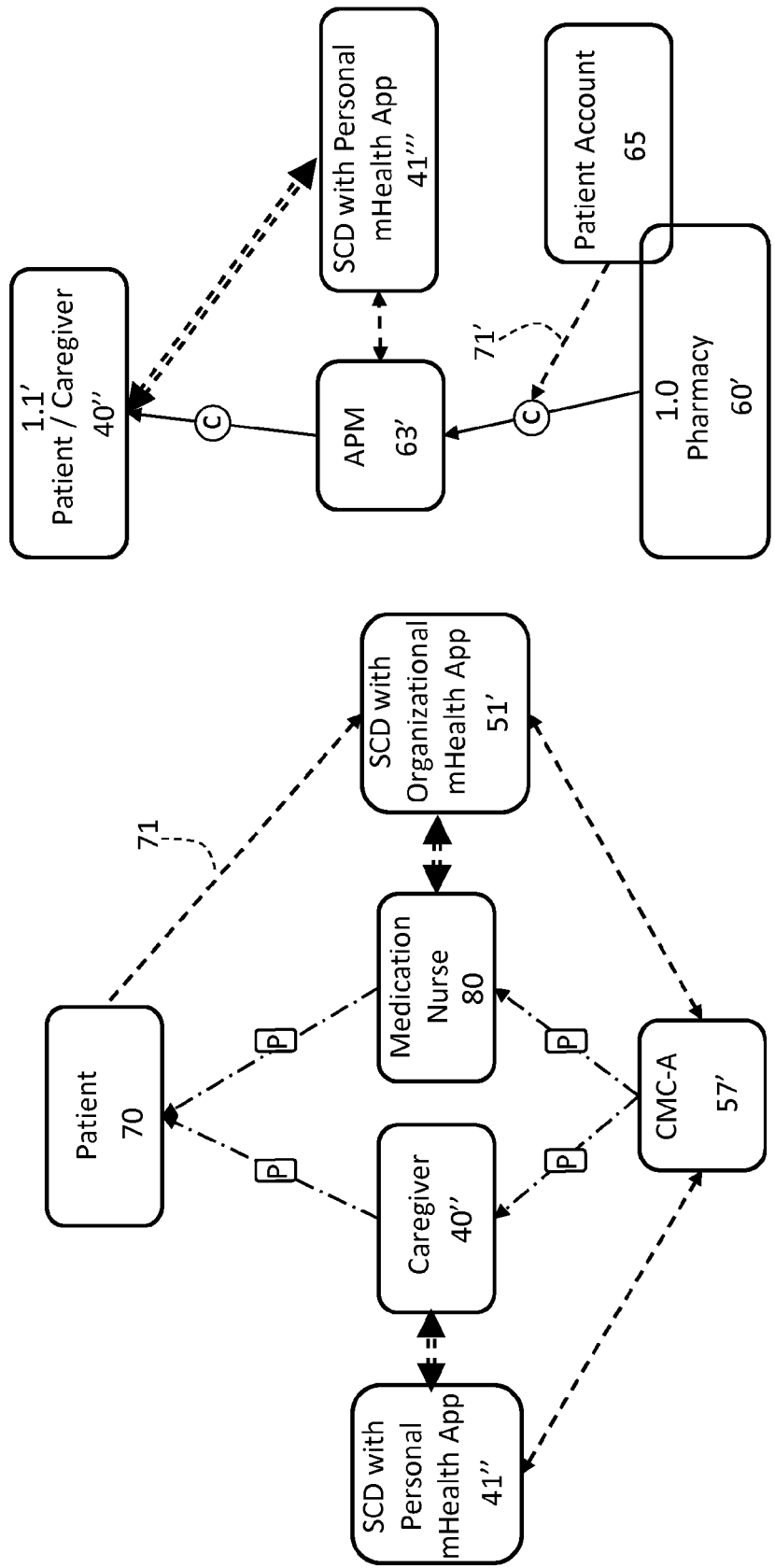

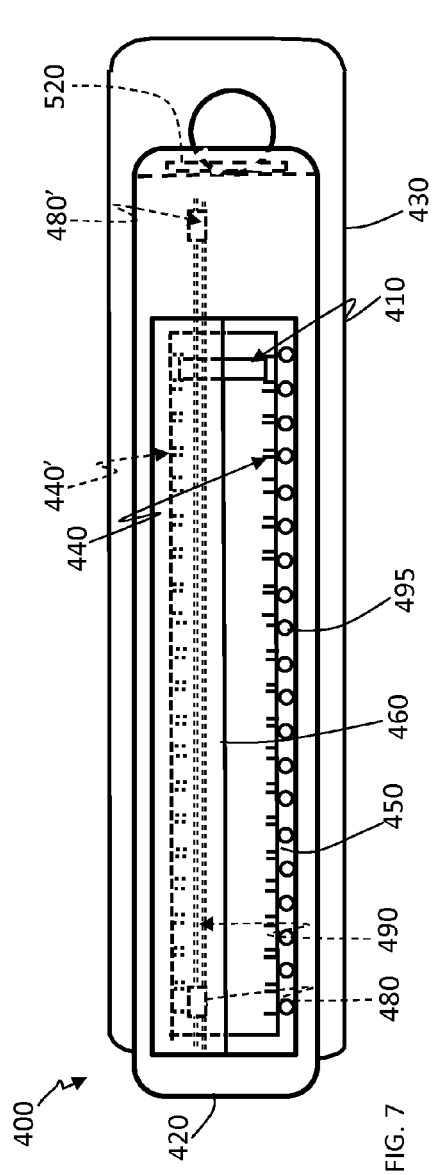
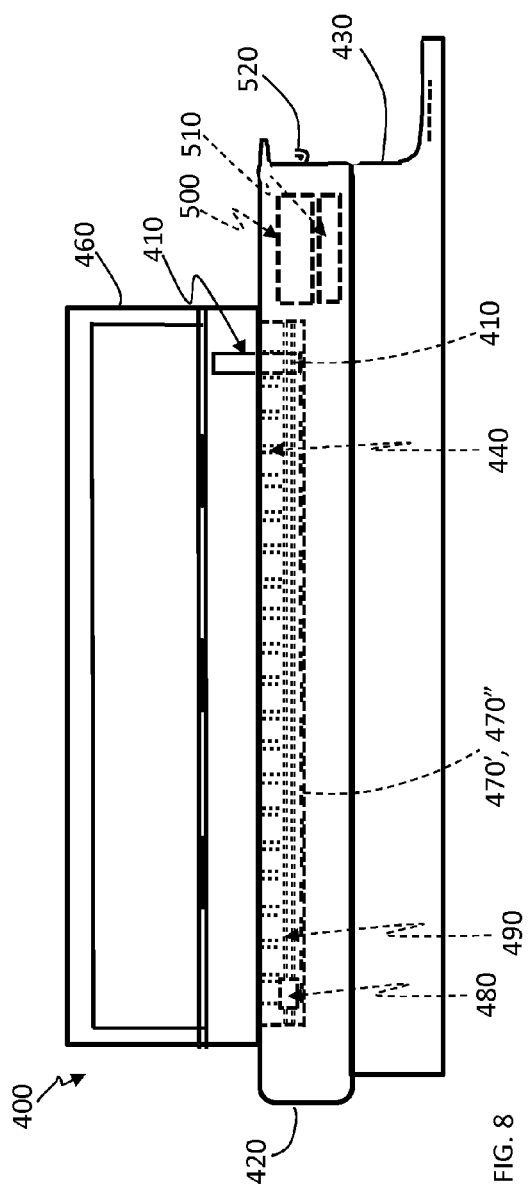

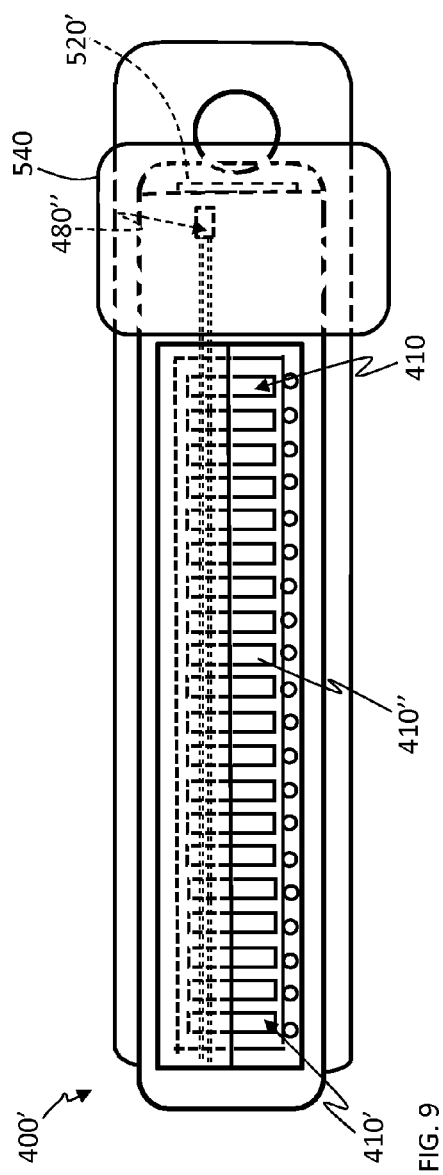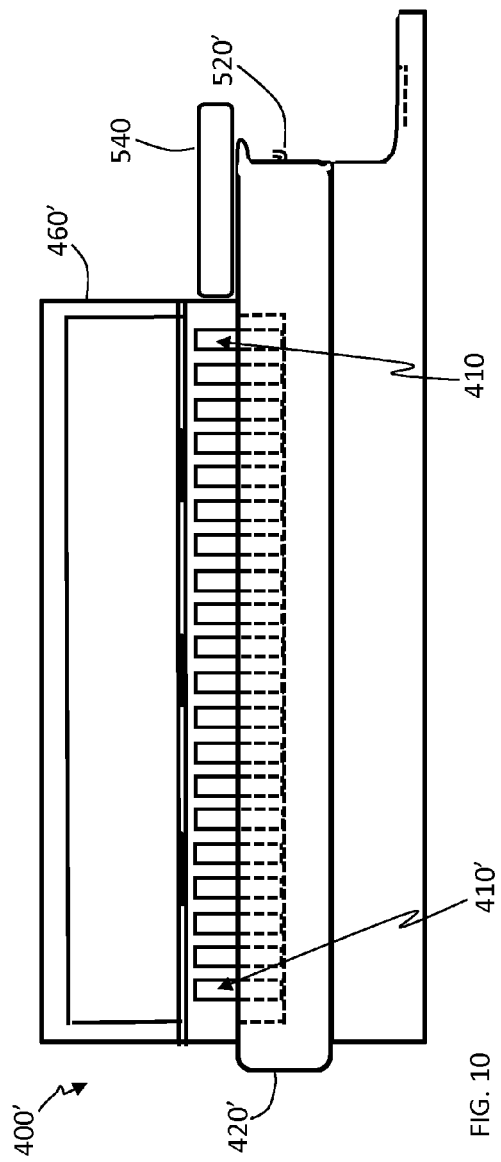

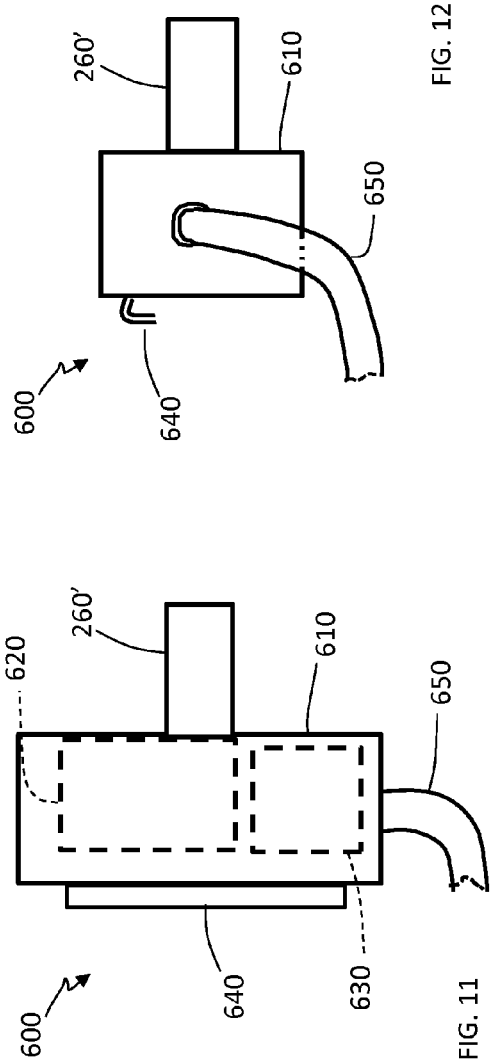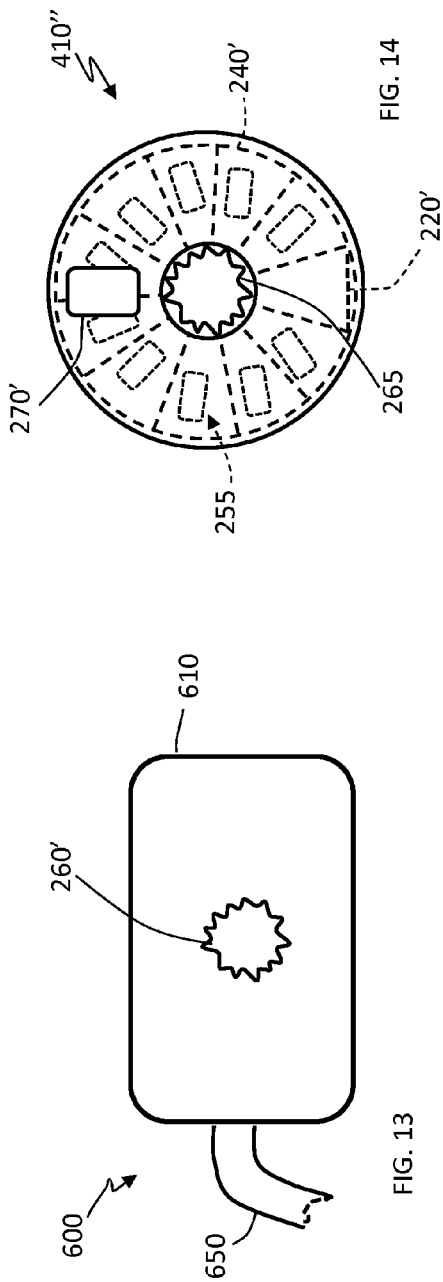

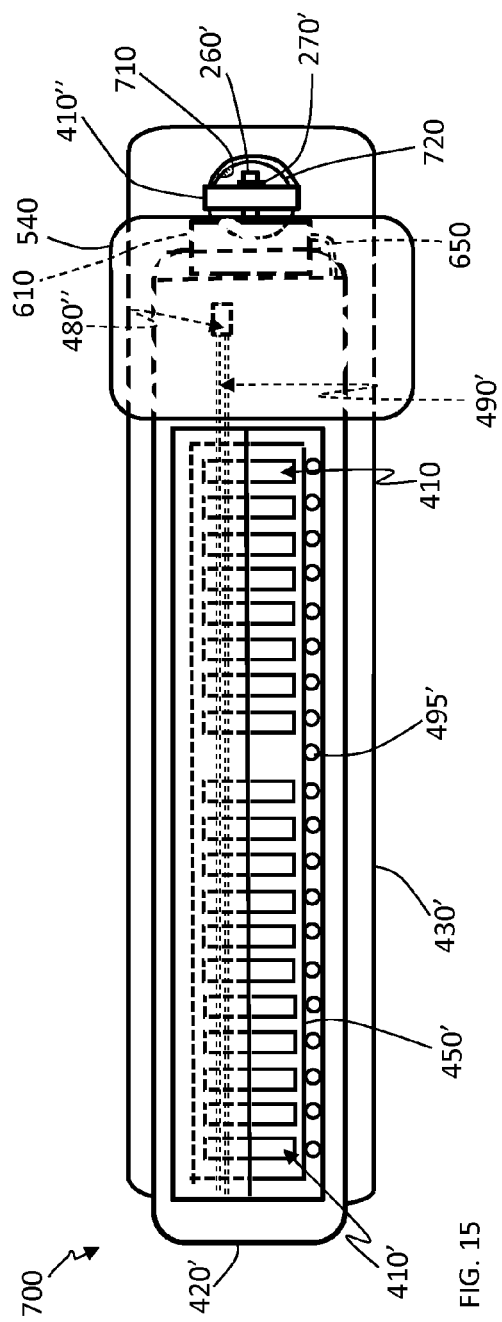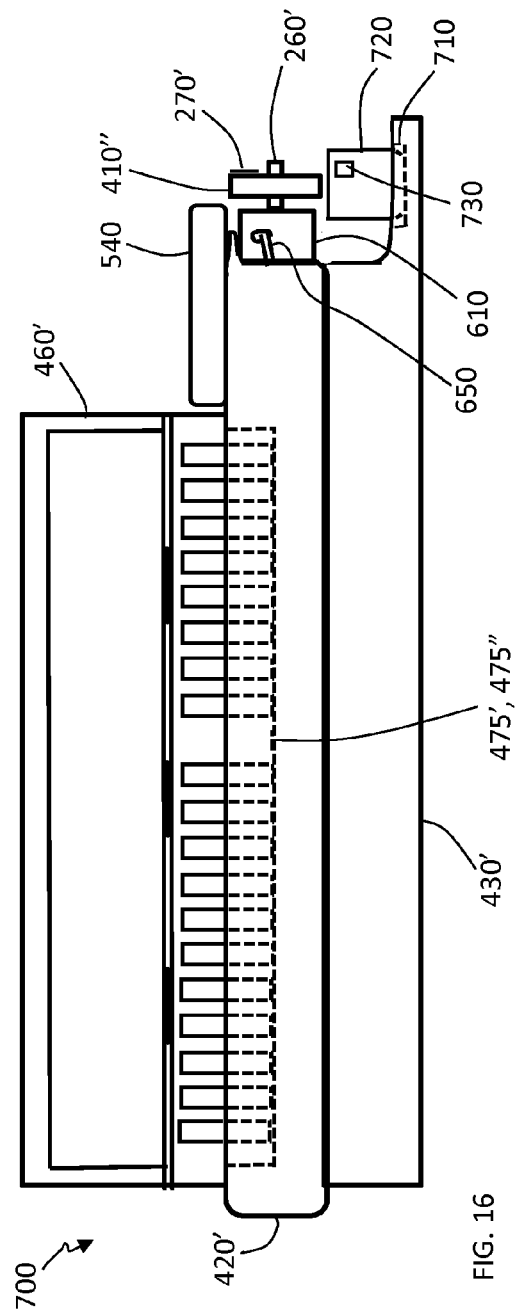

CARTRIDGE-BASED MEDICATION DISPENSING

CROSS-REFERENCE TO RELATED APPLICATIONS

This application claims priority to provisional application 61/897,087 filed on Oct. 29, 2013 and provisional application 62/066,801 filed on Oct. 21, 2014. This application is a continuation-in-part to application Ser. No. 13/204,407 filed on Aug. 5, 2011. The contents of which all three applications are fully incorporated herein with these references.

FIELD OF THE INVENTION

The present invention relates generally to cartridge based digital medication dispensing that improves medication adherence and reduces cost of medication dispensing. More particularly, the present invention relates to multi-cartridge digital dispensing that improves medication adherence with the help of single control device with an application (software application running on a desktop computer, tablet, mobile device or any other like computer) to guide, monitor and control a full cycle of medication dispensing at home setting or health/patient care organization.

BACKGROUND OF THE INVENTION

Mechanical designs of the cartridge based dispensers have been described in U.S. Pat. No. 8,397,946, U.S. Application Ser. No. 61/887,030 and U.S. application Ser. No. 13/204,407. The corresponding disclosures are fully incorporated herein with these references.

The central issue of a medical dispensing is how to provide a comprehensive adherence to a prescription with the presence of myriad of different pills and individual prescriptions involving different pills and cost of medication dispensing. The term "pill" in this disclosure includes pill, tablet or capsule or any solid state form of pharmaceutical or nutraceutical products. The term "medication" includes pharmaceutical, nutraceutical or cosmeceutical products and also any functional food supplements.

Recently, different types of software or computer applications (apps) have been introduced primarily to remind a patient to take medication per programmed in prescription regimen. These applications rely on self-monitoring of the medication taking. The central limitation of these applications is that they do not communicate with a pill dispensing or where it is, as it requires individual prescription programming into pill dispensing device and medication sorting to synchronize pill dispensing with the application.

Another limitation of current digital medication dispensing is that involved medication storing and dispensing devices rely on a network for mutual communication and, as a result are expensive to install and operate as it involves device individual reprogramming to synchronize with changing medication prescriptions.

Thus, there is a great need to provide a system of medication dispensing where monitoring and control is provided by a single control device with a software application/program, say mHealth App, without a need to reprogramming medication dispensing or storing devices themselves with a change in prescription, patient or medication delivery personal or medication availability at a location. The terms "mHealth App" or "App" incorporated any type of software available on mobile device.

SUMMARY OF THE INVENTION

In one embodiment a pill dispensing system includes an electronic mobile communication device having one or more non-transitory computer-readable media having computer executable code stored thereon, where the electronic mobile device includes a wireless transmitter and receiver. A pill cartridge has a cartridge body storing a plurality of pills, where the cartridge body includes an electronic tag storing data. A pill cartridge dispenser is configured to receive at least one of the pill cartridge and configured to electromechanically control dispensing of the plurality of pills from the cartridge body, where the pill cartridge dispenser is configured to be in wireless communication with the electronic mobile communication device. The electronic mobile communication device is configured to wirelessly read the data stored on the electronic tag or wherein the pill cartridge dispenser is configured to wirelessly read the data stored on the electronic tag. The computer executable code includes a routine executable by the electronic mobile communication device to wirelessly communicate with the pill cartridge dispenser to dispense at least one pill from the plurality of pills within the pill cartridge.

In other embodiments, the computer executable code may include a routine executable by the electronic mobile communication device to wirelessly communicate with the passive electronic tag to read the data. The computer executable code may include a routine executable by the electronic mobile communication device to receive a patient dispensing schedule. The computer executable code may include a routine executable by the electronic mobile communication device to process the data from the passive electronic tag with the patient dispensing schedule. The computer executable code may include a routine executable by the electronic mobile communication device to determine when a medication dispensing is needed according to the patient dispensing schedule and data from the passive electronic tag. The computer executable code may include a routine executable by the electronic mobile communication device to register the dispensing of the at least one pill.

The pill cartridge dispenser may be configured to receive a plurality of the pill cartridges.

A loading and tagging machine may be configured to transform the cartridge body, the plurality of pills and a blank electronic tag into a single assembly including the pill cartridge, the plurality of pill and the electronic tag storing data thereby forming the pill cartridge.

The wireless communication between the electronic mobile communication device and the electronic tag or the pill cartridge dispenser may be a short-range wireless technology or a near field communication technology.

The pill cartridge dispenser may be selected from the group consisting of a personal pill dispenser, an active cartridge medication cabinet, a passive cartridge medication cabinet and a passive cartridge medication cabinet with a secondary dispensing module.

The electronic mobile communication device may be selected from the group consisting of a smart phone, an electronic tablet, an electronic wrist watch and a wearable electronic device.

The electronic mobile communication device may be configured to communicate with a centralized database over a wireless intranet or internet.

An automated pharmacy machine may be configured to dispense a pill cartridge to an individual, the individual being a courier, a caretaker or a patient, where the automated pharmacy machine is configured to communicate with the electronic mobile communication device.

A wearable passive electronic tag having patient specific medical information may be configured to be worn or carried by a patient and may be configured to be readable by the electronic mobile communication device.

In an embodiment of a method of dispensing a pill to a patient, the method includes the steps of: providing a pill cartridge enclosing a plurality of pills, the pill cartridge including an electronic tag storing data related to the plurality of pills; placing the pill cartridge into a pill dispensing machine, the pill dispensing machine configured to dispense at least one pill of the plurality of pills from the pill cartridge; providing an electronic mobile communication device having one or more non-transitory computer-readable media having computer executable code stored thereon, the electronic mobile communication device configured to wirelessly communicate with the pill dispensing machine, where at least the electronic mobile communication device or the pill dispensing machine is configured to wirelessly communicate with the electronic tag on the pill cartridge; programming the electronic mobile communication device with a patient pill dispensing schedule; and determining, by the electronic mobile communication device according to the patient pill dispensing schedule, that a medication dispensing is needed; sending a wireless signal from the electronic mobile communication device to the pill dispensing machine instructing the pill dispensing machine to dispense the at least one pill.

Other embodiments may include the step of retrieving the at least one pill by a caretaker and then providing the at least one pill to a patient for consumption of the at least one pill.

Other embodiments may include the step of registering the dispensing of the at least one pill by the patient to the electronic mobile communication device.

Other embodiments may include the step of providing a patient with a wearable passive electronic tag having patient specific medical information.

Other embodiments may include the step of wirelessly communicating by the mobile electronic device with the wearable passive electronic tag to read the patient specific medical information and then comparing that with the patient pill dispensing schedule and data related to the plurality of pills.

Other embodiments may include the step of providing a loading and tagging machine configured to transform a cartridge body, the plurality of pills and a blank electronic tag into a single assembly including the pill cartridge with the electronic tag storing data, wherein the electronic mobile communication device is configured to wirelessly communicate with the loading and tagging machine.

The pill dispensing machine may be configured to receive a plurality of pill cartridges.

The electronic mobile communication device may be configured to be programmed with a plurality of different patient pill dispensing schedules, and wherein the electronic mobile communication device may be configured to communicate with a plurality of pill dispensing machines corresponding to the plurality of different patient pill dispensing schedule, each pill dispensing machine having its own respective pill cartridge or plurality of pill cartridges.

Another embodiment of pill dispensing system may include an electronic mobile communication device having one or more non-transitory computer-readable media having computer executable code stored thereon, where the electronic mobile device includes a wireless transmitter and receiver. There are a plurality of pill cartridges, each pill cartridge including a cartridge body storing a plurality of pills, where the cartridge body includes an electronic tag storing data, where the electronic mobile communication device is configured to wirelessly read the data stored on the electronic tag. A pill cartridge dispensing machine is configured to receive the plurality of pill cartridges and configured to electromechanically control dispensing of the plurality of pills from the cartridge body, where the pill cartridge dispensing machine is configured to be in wireless communication with the electronic mobile communication device. The computer executable code may include: i) a routine executable by the electronic mobile communication device to wirelessly communicate with the electronic tag to read the data; ii) a routine executable by the electronic mobile communication device to receive a patient dispensing schedule; iii) a routine executable by the electronic mobile communication device to process the data from the electronic tag with the patient dispensing schedule; iv) a routine executable by the electronic mobile communication device to determine when a medication dispensing is needed according to the patient dispensing schedule and data from the electronic tag; and v) a routine executable by the electronic mobile communication device to wirelessly communicate with the pill cartridge dispensing machine to dispense at least one pill from the plurality of pills within the pill cartridge.

Another embodiment of a pill dispensing system includes an electronic mobile communication device having one or more non-transitory computer-readable media having computer executable code stored thereon, where the electronic mobile device includes a wireless transmitter and receiver. A pill cartridge has a cartridge body storing a plurality of pills, where the cartridge body includes an electronic tag storing data. A loading and tagging machine is configured to transform the cartridge body, the plurality of pills and a blank electronic tag into a single assembly including the pill cartridge, the plurality of pill and the electronic tag storing data thereby forming the pill cartridge. The electronic mobile communication device is configured to wirelessly communicate with the loading and tagging machine. The computer executable code includes a routine executable by the electronic mobile communication device to wirelessly communicate with the loading and tagging machine to electromechanically dispense at least one pill cartridge.

A pill cartridge dispenser may be configured to receive at least one of the pill cartridge and may be configured to electromechanically control dispensing of the plurality of pills from the cartridge body, where the pill cartridge dispenser may be configured to be in wireless communication with the electronic mobile communication device.

The electronic mobile communication device may be configured to wirelessly read the data stored on the electronic tag or wherein the pill cartridge dispenser is configured to wirelessly read the data stored on the electronic tag, and wherein the computer executable code includes a routine executable by the electronic mobile communication device to wirelessly communicate with the pill cartridge dispenser to dispense at least one pill from the plurality of pills within the pill cartridge.

Another embodiment of pill dispensing system includes an electronic mobile communication device having one or more non-transitory computer-readable media having computer executable code stored thereon, where the electronic mobile device includes a wireless transmitter and receiver. There are a plurality of pill cartridges, each pill cartridge including a cartridge body storing a plurality of pills, where the cartridge body includes an electronic tag storing data. An automated pharmacy machine stores the plurality of pill cartridges, where the automated pharmacy machine is configured to dispense at least one pill cartridge to an individual, the individual being a courier, a caretaker or a patient. The automated pharmacy machine is configured to communicate with the electronic mobile communication device. The computer executable code includes a routine executable by the electronic mobile communication device to wirelessly communicate with the automated pharmacy machine to electromechanically dispense at least one pill cartridge.

A pill cartridge dispenser may be configured to receive at least one of the pill cartridge and may be configured to electromechanically control dispensing of the plurality of pills from the cartridge body, where the pill cartridge dispenser may be configured to be in wireless communication with the electronic mobile communication device.

The electronic mobile communication device may be configured to wirelessly read the data stored on the electronic tag or wherein the pill cartridge dispenser may be configured to wirelessly read the data stored on the electronic tag, and wherein the computer executable code may include a routine executable by the electronic mobile communication device to wirelessly communicate with the pill cartridge dispenser to dispense at least one pill from the plurality of pills within the pill cartridge.

BRIEF DESCRIPTION OF THE DRAWINGS

The accompanying drawings illustrate the invention. In such drawings:

FIG. 1 introduces graphical definitions of symbols used in describing the method of the cartridge-based medication dispensing;

FIG. 3 graphically demonstrates medication dispensing by the secondary dispensing;

FIG. 4 graphically demonstrates medication dispensing via APM referenced to in FIG. 2 as option 1.0;

FIG. 7 shows a top view of the cartridge medication cabinet in storage format, i.e. passive form abbreviated as CMC-P;

FIG. 8 shows a side view of the CMC-P 400 with open cover to show a position of one of the cartridges stored in the storage compartment;

FIG. 9 demonstrates a top view of CMC-P similar to one on FIG. 7 but with the full load of cartridges;

FIG. 10 demonstrates a side view of the same device from the FIG. 9;

FIG. 11 demonstrates a top view of a secondary dispensing module (SDM);

FIG. 12 demonstrates a side view of the secondary dispensing module shown on the FIG. 11;

FIG. 13 demonstrates a front view of the secondary dispensing module shown on the FIG. 11;

FIG. 14 demonstrates a front view of one of the cartridges stored in the CMC-P 400' shown on the FIG. 9;

FIG. 15 demonstrates a passive cartridge medication cabinet (CMC-P) from FIG. 9 with the attached secondary dispensing module (SDM) from FIG. 11 to form an active cartridge medication cabinet (CMC-A); and FIG. 16 demonstrates a side view of the CMC-A 700 with the cover open for a cartridge access.

DETAILED DESCRIPTION OF THE PREFERRED EMBODIMENTS

Figure 2:
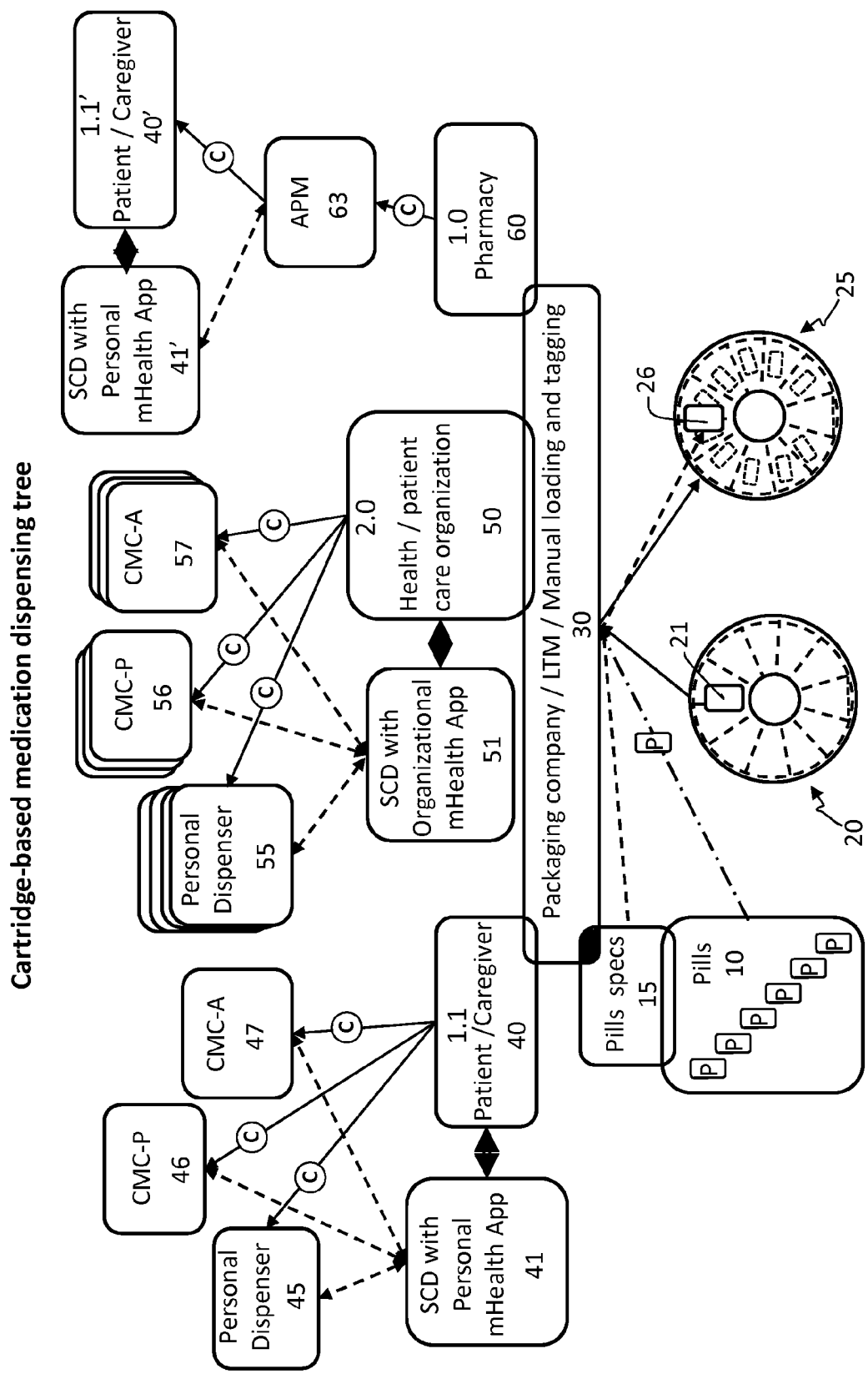
FIG. 2 graphically demonstrates an embodiment of a method of the invention which is a so called cartridge-based medication dispensing tree.

An embodiment of the invention discloses a method of medication dispensing and the devices involving in a dispensing cycle that utilize standard unidose prefilled cartridges as the common form of the medication dispensing in place of myriad of pills. Cartridge has been described in U.S. Pat. No. 8,397,946 as a set of compartments where the medication is distributed at and it also includes a blister pack consisting of a set of cavities or pockets made from a formable web, usually a thermoformed plastic but could include other formable materials. Term "unidose" means the same medication fills a single cartridge. The unidose prefilled cartridges allow standardization of the variety of pills and prescriptions because all cartridges have the same physical form and includes communication tag to carry all medication info of the pills filled the cartridge as disclosed in the U.S. application Ser. No. 13/204,407, i.e. name, dose, expiration, manufacturer and so on. There is also an option to include patient info, i.e. Patient ID, DOB (date of birth) and so on as part of the tag data which can be added to the same tag or an additional tag.

The prefilled and tagged cartridge allows the conversion of a pill-based medication dispensing with its variety of shapes and forms into standardized cartridge-based medication dispensing that is monitored from the initial step of wholesale pill distribution for filling the cartridge to the final step of the pill taking by a patient. The term "cartridge" in the present invention is used in reference to prefilled and tagged cartridge. Otherwise, the term "empty cartridge" is referenced herein.

One embodiment of the invention is to use short-range wireless (SRW) technology based Integrated Circuits, i.e. Bluetooth, Wi-Fi, ZigBee, NFC, etc. for M2M (machine to machine) communication utilizing a mobile single control device (SCD) (all called an electronic mobile communication device) throughout all steps involved in the medication dispensing for guidance, monitoring and control. The embodiment may include the use of NFC (near field communication) technology. NFC allows for Reader mode where active NFC device reads a passive tag that does not require a power (one-way communication) and P2P (peer to peer) mode (two-way communication) between NFC-enabled devices, i.e. the devices that include NFC chips. The P2P technology allows transfer information from one device to another directly, without using a wireless network. The term "tag" is used in the present invention in reference to a programmed tag and "chip" is used in reference to NFC chip.

Thus, one embodiment of the invention may incorporate a mobile single communication device, SCD as a smart phone or tablet or wearable device for instance, to guide, monitor and control all steps of medication dispensing including pill dispensing, pill storing and pill secondary dispensing by communicating with tags and chips of the units involved in the full cycle of a medication dispensing. The guiding, monitoring and control are performed via an application (mHealth App) installed on the SCD and all communication with different devices is conducted via the SCD. One possible advantage (but not necessarily required advantage) of the disclosed method is that a single update of the application (mHealth App) of SCD allows changing the medication dispensing regimen without a need to interact with multiple units involved in the cycle. Besides, allocating the SCD to a single person responsible for medication dispensing allows to individualize responsibility for a medication dispensing which is important aspect of the medication adherence program.

There are several options for communicating between the cartridge-dispenser system and the application on a mobile device. In both options the cartridge includes a tag to store data on the medication placed into the cartridge, for instance NFC tag or general RF tag. Also in both options the communication is established between the dispenser and application on the mobile device, for instance low voltage Bluetooth or could be other type of wireless communication. One option is the dispenser includes the tag reader to read in the cartridge tag data in and the other option is to have the application on the mobile device to read in the cartridge tag data before the cartridge is placed into the dispenser and/or after the cartridge is placed into the dispenser. The second option involves the additional step but it allows to reduce a cost of the dispenser by eliminating the tag reader at the dispenser.

The present method also discloses the process of controlled medication dispensing in different medication dispensing environments, such as, (1) personal medication dispensing from a pharmacy, i.e. personal medication dispensing with or without home caretaker assistance, or (2) organizational medication dispensing, i.e. health/patient care organizations such as hospitals, nursing homes, assistant living homes, etc.). A mobile SCD, such as a smart phone, is used for either a personal or organizational medication dispensing. In later case, each mobile SCD is assigned to one trained person, called for instance a "medication nurse", to perform monitoring and control the medical dispensing for the patients assigned to the medication nurse care. The advantage of the present method is to allow tracking a quality of the person's operation throughout all steps of medication dispensing within the organization. The present method allows guiding, monitoring and control medication dispensing of all three aspects involved: (a) medication dispensing itself in terms of right dose at right time, (b) activities in terms of medication dispensing of a medication nurse who performs the medication dispensing and (c) patient in terms of verification that the medication is dispensed to the right patient.

The method may involve a "Loading and Tagging Machine" (LTM) to assist in placing pills into a cartridge and labeling the cartridge by programming the tag. Another embodiment of the invention describes a central operational part of the LTM for loading pills into cartridge and programming the tag of the cartridge with pill information.

Personal dispensing by a patient himself or with a help of a caregiver is offered by a cartridge-based dispenser described in the U.S. Pat. No. 8,397,946 and U.S. Application Ser. No. 61/887,030. Dispensing a large number of different medications particularly to a number of patients may be performed by including a number of pill dispensers assigned to a given patient. Another option is to utilize a secondary dispensing which is particularly useful in an organizational setting where the personnel such as medication nurse, is available. Secondary dispensing is defined as a process of collecting prescribed pills from multiple unidose cartridges without involving pill dispensers into a patient cup for consecutive pills dispensing to the patient, i.e. it includes a separate step in the medication dispensing cycle which also requires individual guidance, monitoring and control. It leads to another embodiment of the present disclosure describing a device, called "Cartridge Medication Cabinet—Active" (CMC-A) to guide, monitor and control secondary dispensing from a large number of unidose cartridges.

The method to guiding, monitoring and controlling medication dispensing also recognizes the need to monitor medication storage in terms of controlling the medication availability, i.e. to insure that the required medication is available, how many unites are available and so on. The storage control is also conducted per the disclosed method with single control device (SCD) via the application (mHealth App). This leads to another embodiment describing the cartridge storage device for cartridge-based medication called "Cartridge Medication Cabinet—Passive" (CMC-P). The referenced above CMC-A device is of the modular structure with the CMC-P being one module and another module being added for a secondary dispensing and called "Secondary Dispensing Module" (SDM). CMC-A, CMC-P and SDM are all NFC enabled devices to be controlled via an application (mHealth App) residing on mobile single control device (SCD)

The method to guide, monitor and control medication dispensing also recognizes the need to make medication dispensing more cost effective for a pharmacy and patients in a personal dispensing. Pharmacy working hours are usually limited thus creating a potential issue to collect medication particularly by a full time working person. Additionally, significant resources are allocated by a pharmacy for sales transactions. Cartridge-based medication dispensing allows to overcome these limitations by introducing "Automated Pharmacy Machine" (APM) which a pharmacy loads with cartridges of prescribed medications for a patient or assigned to the patient for "any-time" pick up.

The standardization of the cartridges leads to uniformity of their packaging which together with electronic tag for medication labeling, allows for autonomous operation analogous to a bank ATM but applied to a cartridge with medication. The method of cartridge-based medication dispensing allows placing multiple APMs at different locations to complement a centralized pharmacy for a medication distribution. This is particularly suitable for refills where a consultation with pharmacy is not usually required. The application (mHealth App) may provide a patient with all necessary safety and effectiveness info on a medication and also allows for a "chat" communication with a pharmacy's assigned person or a direct call communication with the pharmacy as a patient has been already authenticated by the application (mHealth App).

FIG. 1 introduces graphical definitions of symbols used in describing the method of the cartridge-based medication dispensing. The symbols of "pill", "tag" and "cartridge" transfers include a physical transfer of a pill or cartridge with tag. The graphical definition also lists different options of data transfers such as data input, data one-way and two-way transfers. The symbols may be combined, for instance, cartridge transfer may include symbol of "prefilled cartridge with programmed tag".

FIG. 2 graphically demonstrates an embodiment of a method of the invention which is a so called cartridge-based medication dispensing tree. The "tree" starts with the loading loose pills 10 into blank cartridge 20 with blank programmable tag 21 to be performed either by a packaging machine at the pill manufacture or separate packaging company, or by a "Loading-Tagging Machine" (LTA) or manually, block 30. The process also includes tagging, i.e.

programming the tag with the information about the pill, block 15. The conversion is shown graphically as a transfer the combination of empty cartridge 20 with blank tag 21, set of pills (medication) 10 and their spec (name, dose, manufacturer, expiration date, etc.) 15 into the single unit of the prefilled cartridge 25 with the programmed tag 26 incorporating the pill specs. The term "loading" means filling a cartridge with pills and the term "tagging" means programming a tag that is placed at the cartridge with the information about the pills for communication with the application (mHealth App) or a functionally equivalent software program. Tagging can be performed by different means such as at a packaging machine such as LTM or different type of packaging machine or by a separate tag writing device.

All pills of the cartridge have the same specification and the corresponding cartridge is called a unidose cartridge. Conceptually, it might be different pills, i.e. multidose cartridge but it complicates the process of medication dispensing with a standardized cartridge. There is also option to include patient info such as ID, Patient specific identifiers (DOB, etc.) to the tag or to a separate tag for patient person personalization of the cartridge based medication dispensing in addition to the standardization.

The "tree" shows that the medication dispensing can at least be done in three options, i.e. tree branches:

(1) home setting by a patient or caregiver which is referenced to as 1.1 option; (2) within a health or patient care organization which is referenced to as 2.0 option; and (3) within a pharmacy which is called 1.0 option which is the addition to the option 1.1. The "tree" demonstrates a physical transfer of a prefilled and tagged cartridge to each cartridge holding unit within each option 1.1, 2.0 or 1.0 under guidance, monitoring and control of corresponding application (mHealth App) residing on SCD.

In 1.1 option, the patient/caregiver 40 input the patient's prescription data into personal application (mHealth App) resided on SCD 41. For instance, a smart phone acts as SCD and a number of models are NFC-enabled devices to allow for secure communication with a tagged cartridge. The cartridge filing can be done manually or by personal LTM. This option assumes personal, i.e. in home, pill to cartridge transfer and the SCD can be used to write (program) the tag of the cartridge for medication specs and also for Patient ID/Patient specific identifiers. The data input into the personal application (mHealth App) might be also performed by a pharmacy with the electronic data transfer from a medical provider thus further reducing a chance of error. As shown by 1.1 option, the personal application (mHealth App) resides on SCD initiates and monitors a loaded (prefilled) and tagged cartridge transfer to a personal or pill dispenser 45 for pill dispensing or CMC-P 46 for cartridge storage or CMC-A 47 for secondary pill dispensing. As a pill is dispensed from the personal dispenser 45, the event is guided, monitored and recorded by the application (mHealth App) resided at the SCD 41. As a cartridge is removed from CMC-P 46, the event is also guided, monitored and recorded by the application (mHealth App) residing at the SCD 41. As a secondary dispensing is performed by CMC-A 47, the event is also guided, monitor and recorded by the application (mHealth App) residing at the SCD 41.

Description of NFC is disclosed herein. There is "Reader mode" allowing the NFC-enabled device to read a tag and "P2P mode" allowing the NFC-enabled device to exchange information with other NFC-enabled device. An NFC-enabled device may also "write" data into the tag. For instance, the SCD writes the tag in conversion from pill form to cartridge form of the medication dispensing, or SCD read the cartridge tag for the data on medication placed into the cartridge. The central point of the disclosed method is that the SCD communicates with tags and all other NFC-enabled devices such as a Personal Dispenser for pills dispensing to guided, monitored and controlled. CMC-P for cartridge storage is also for guided, monitored and controlled dispending (the explanation is provided below) or CMC-A is for guided, monitored and controlled dispensing of the secondary dispensing where a medication (a pill) is initially dispensed into a carrier (cap, for instance) for consecutive dispensing from the carrier to a patient. In this respect, a personal pill dispenser can be called "direct pill dispenser" where medication dispensing is conducted directly to a patient.

NFC Interaction is based on a message/reply system. A device that begins the interaction process is called the "initiator" and the other called the "target" and SCD is always the "initiator". SCD sends a message to a device A as a target, device A then responds as the device A cannot send data without being contacted first by the initiator. The important advantage is that NFC forgoes the "pairing" process between NFC-enabled devices entirely contrary to other M2M technologies (Bluetooth, WiFi). Thus NFC-enabled SCD allows automatic "pairing" and effortless communication and control of data transfer and, as result, monitoring and control pills dispensing via cartridges. In terms of security and interference with other devices, NFC-enabled SCD benefits from the condition that maximum working distance is less than 20 cm and usually within only 4 cm. Therefore, SCD initiates the dispensing devices only in a very close proximity to provide data exchange for monitoring and controlling the medication dispensing cycle. There are other communication methods that pair (like RFID, ZigBee, optical barcode, and mentioned above Bluetooth, WiFi) which can also be used in communication and all of them are included under the referencing to NFC-communication for generality.

Option 2.0 it involves a cartridge-based medication dispensing within a health or patient care organization 50. An assigned person first inputs data of the patient's prescriptions of the facility patients into a file at a centralized organizational location (such as an intranet or the Internet) to serve as an input to the organizational application (mHealth App) residing on all SCD 51 individually assigned to medication nurses. The data may be electronically transferred to the centralized organizational location from all the medical providers involving in patient care of a given health or patient care facility. Patient IDs are also assigned for real time tracking and can be then programmed into the cartridge tag during pill filling/tag programming process during pill to cartridge conversion.

A remote cloud based server (HIPAA compliant) (intranet/Internet) can be used to store the information, and one can use a more fault tolerant distributed DB model (eg Hbase) to make data processing scalable for organization medication dispensing, so called "enterprise applications". Similar to a personal medication dispensing, an application (mHealth App) on SCD 51 of the organization medication dispensing guides, monitors and controls all CMC-P 56 for cartridge storage or all LMC-A 57 for secondary dispensing or multiple personal pill dispensers 55 as another option for pill storage and dispensing. The option 2.0 demonstrates physical transfer of cartridges to each device (cartridge holding unit) with the application (mHealth App) on SCD to provide full monitoring and control of all transfers. There could be a number of "medication nurses" within the organization each with assigned SCD to manage medication dispensing allocated to each medication nurse patients to allow for the individual monitoring and responsibility awareness of a medication nurse.

Option 1.0 involves a pharmacy 60 where cartridge-based medication dispensing offers flexibility for medication dispensing via Automated Pharmacy Machine (APM) 63 explained in more details in a following figure. The option 1.0 demonstrates that a pharmacy 60 loads a number of cartridges into an APM 63 for a distribution to a patient 40' which then follows medical distribution branch 1.1' that is equivalent to the option 1.1 described above.

FIG. 3 graphically demonstrates medication dispensing by the secondary dispensing referenced to in the FIG. 2 as 47 and 57. The process is also guided, monitored and controlled by the corresponding application (mHealth App's) residing at SCDs 41" and 51'. In case of a personal medication dispensing, a caregiver 40" or patient enters time of medication dispensing into personal application (mHealth App) on SCD 41". In case of an organizational medication dispensing, a medication nurse 80 used assigned SCD 51' to read in patient's tag from, say, patient wearable device, wrist band for instance of the patient 70, for patient ID (71) verification to ensure that the right patient is dealt with for a medication dispensing and then enters time of the medication dispensing into the application. The confirmation of medication intake may can be tactile in the application (using gestures, etc), and actual time recorded would be automatically time stamping. The described organizational medication dispensing cycle allows guiding, monitoring and control from the initial step of the pills placement into the cartridges to the final step of the medication taking.

FIG. 4 graphically demonstrates medication dispensing via APM 63' referenced to in the FIG. 2 as option 1.0. A patient 40" establishes patient's account 65 at the pharmacy 60' for communication and authentication. The account 65 includes patient ID and other info. Upon a patient's request for a prescribed medication, the pharmacy 60' transfers pills into cartridges and program their tags with medication specs and patient ID 71' from the account 65. Then the prefilled and tagged cartridge is placed in an APM 63'. An APM 63' can be located at the pharmacy location for "any-time" medication pickup or at a different APM location closest to the patient's address indicated in the patient's account. In general, an organization other than a pharmacy may be responsible in handling cartridges and a more general terms "cartridge handling organization" is used to reference to any such organization including a pharmacy.

Thus, the cartridge includes programmed tag or tags with patient ID together with the medication specs. The NFC reader of the APM 63' scans the cartridges to correlate their locations in the APM 63' with the Patient IDs. At any time, patient 40''' initiates communication with NFC-enabled APM 63' to authenticate the personal application (mHealth App) on his or her SCD 41''' to request a cartridge release from the location assigned to the Patient ID. Upon a cartridge pickup, the follow up steps of medication dispensing process fall under the Option 1.1 described in the FIG. 2. The difference from the description of the method under the Option 1.1 is that the cartridges have been provided by the pharmacy instead of the pill to cartridge conversion at patient's or caregiver location.

A similar process can be applied to an organizational medication dispensing where an APM is located at the organization premises for a medication nurse collecting cartridges for medication dispensing using assigned SCD with organizational application (mHealth App). An APM operation can be conducted by a centralized pharmacy or a section of the organization responsible for loading and tagging the cartridges per patient's prescriptions. Regardless of a logistical arrangement, the described method of cartridge-based medication dispensing allows for consistent process of a real-time monitoring and control by the application (mHealth App) due to standardized cartridge.

As the addition note, the cartridge based medication dispensing is cost effective option for over the counter (OTC) products where a manufacturer provides an OTC medication in the cartridge form. An OTC cartridge is loaded into APM for any-time purchase. In this case a patient does not require to establish a patient account. It is convenient, cost effective and safer to have a communication with APM via personal application (mHealth App) on SCD device for OTC product specification communication where the application can scan the product available at the APM and instantly review an intended for purchase OTC product for its expiration date, effectiveness and safety, including any contraindication with other medication taken by the User (patient) that had been prior inputted into the personal application (mHealth App). It also allows a cost effective tracking a usage of OTC products with the option to track the Users in terms of their conditions if they allow for such monitoring.

Figures 5, 6:
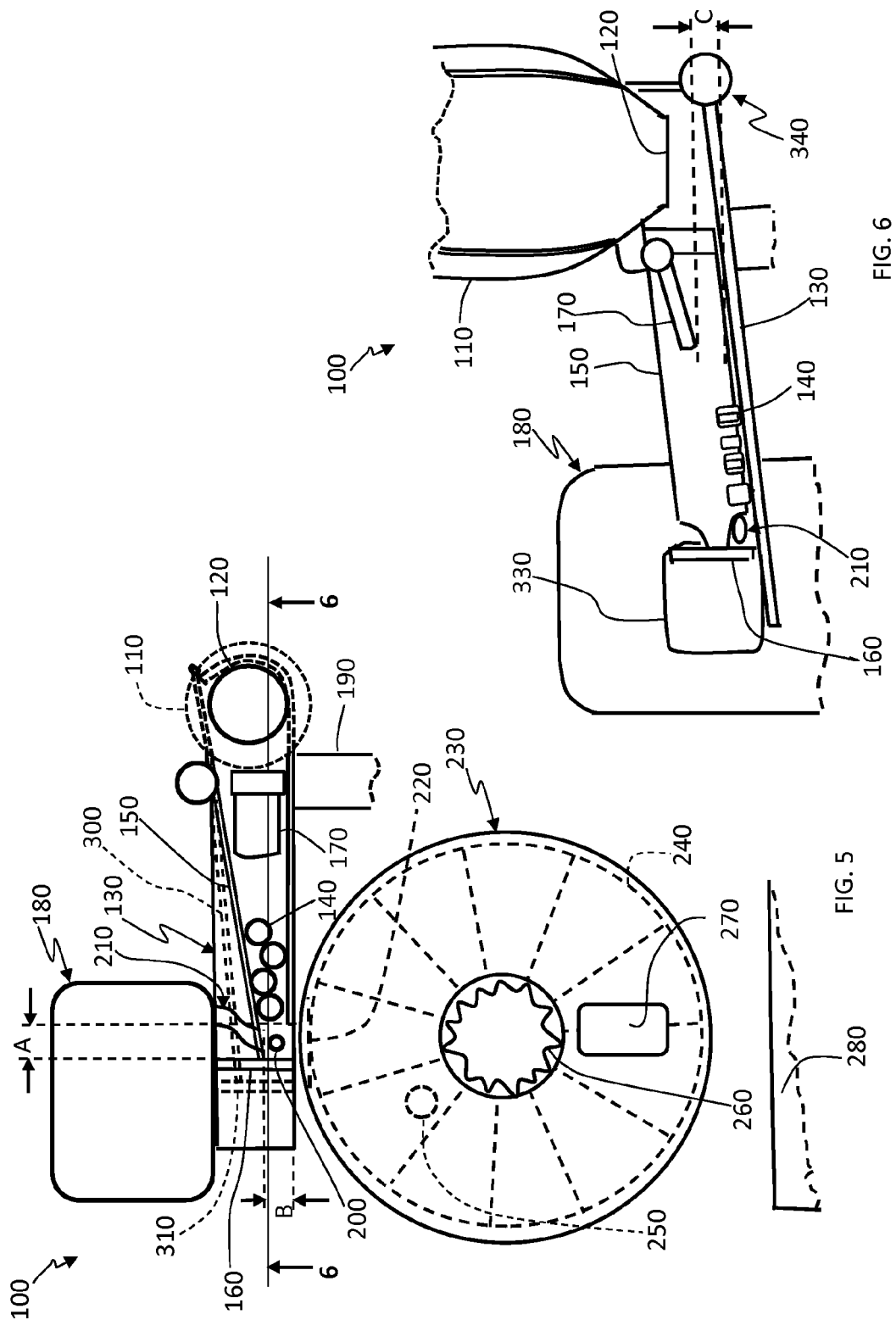
FIG. 5 demonstrates a top view of one embodiment of loading-tagging machine for filling a cartridge with pills and programming (writing) attached to the cartridge tag.
FIG. 6 is a side view of the loading-tagging machine with reservoir and opening for dropping the pill and others onto the transporter.

FIG. 5 demonstrates a top view of one embodiment of loading-tagging machine (LTM) 100 for filling a cartridge with pills and programming (writing) attached to the cartridge tag. The pills of single type of medication are placed into the reservoir 110. The pills drop through the opening 120 onto the transporter 130 represented by a thin plate tilted down at the other end and vibrating for the pill 140 and others to slide down toward the cartridge 230. The path of the pills is controlled and their movement is directed by three elements: (a) tongue 170 to insure that no pill is on the top of the other pill, i.e. a single layer of pills is present and (b) that only a single pill reaches the end of the transporter 130 before its loading into the cartridge 230. The (b) condition is controlled by the adjustable side wall 150 and adjustable bottom wall 160. The LTM electronic memory contains the pill specs including pill's 3D dimensions to allow for accurate adjustments. Before the pill transporting towards the cartridge, the tongue 170, side wall 150 and bottom wall 160 are adjusted. For instance, based upon the pill dimensions, the side wall is adjusted to the space B and bottom wall for the space A to insure that only a single pill reaches the end of the transporter 130.

As the pill reached the end of the transporter 130, i.e. contact the bottom wall, it blocks the photocell 200, thus registering that the pill reached the end position at the transporter 130. This activates the air jet through the tube 210 to blow the pill through the cartridge opening 220 into the segment of the receptacle 240. The photocell 200 momentarily becomes open and this activates the immediate rotation of the rotating shaft 260 to rotate receptacle 240 to the next segment position at the cartridge opening 220 to insure that only one pill is placed at the segment. For instance, pill 250 was placed in the segment at the prior step and the following segment is available to receive the next pill.

The member 180 is a mechanical unit to control side and bottom walls adjustments. For instance, they can be adjusted for different positions such as 300 and 310 correspondingly. Another member 190 is also a mechanical unit to adjust the tilt of the tongue 170.

There is also a NFC writer 280 to program the tag 270 for the pill specs and optionally for patient information of a patient the pill are prescribed to. The tag may also include information on the cartridge such as a number of segments, so called storage compartments, for communicating with a LTM and possibly a dispensing unit.

The tag programming occurs during some point of the cartridge loading. There is an option to use SCD, NFC-enable smart phone for instance, as NFC writer in the LTM as a cost effective solution of tagging the cartridge in LTM which is particularly useful in case of home care, option 1.1 of the FIG. 2. The personal application (mHealth App) on the SCD can also be used as the NFC writer in the personal LTM to control the dispensing cycle and also to reduce cost of the LTM for personal use.

If SCD is not used as NFC writer in the LTM, the LTM can still be NFC-enabled device and a separate SCD initiates communication with its NFC chip for SCD's application (mHealth App) to control the loading and programming process, i.e. adjustment of the tongue 170 and walls 150, 160 positions and program the tag for medication specs. The data on a number of cartridge segments may reside at the LTM memory to control a number of the rotation steps to fill in the cartridge and switching to an empty cartridge for another loading and tag programming. In terms of switching the cartridges, the option is to have a stack of cartridges on the rotating shaft 260 and the shaft moves up or down upon loading the cartridge to the next empty cartridge in the stack. All cartridges are placed with the cartridge opening 220, etc. facing the opening of air-jet tube 210.

FIG. 6 is a side view of the loading-tagging machine (LTM) 100 with reservoir 110 and opening 120 for dropping the pill 140 and others onto the transporter 130. The transporter 130 is tilted down and vibrated by the mechanism 340 for pill movement towards other end of the transporter 130. The tongue 170 is shown as a rotating plate to control a height of opening C between the tongue 170 and transporter 130 which is also provided by the 3D data of the pill stored at the memory. There is also a side wall 150 and a bottom wall 160. The FIG. 6 also shows opening of the air-jet tube 210. The mechanical unit 180 includes the opening 330 within which the bottom wall 160 is adjusted. The side wall 150 is connected and adjusted along the bottom wall 160 by the mechanical unit 180.

Thus, the disclosed method of cartridge loading and programming includes: placing NFC-enabled device with read/write capability next to the loading cartridge location at the pill loading machine within a working distance to the cartridge tag and placing an empty cartridge with blank tag in the cartridge loading location and placing loose pills of the same medication in the machine; the application (mHealth App) of NFC-enable device SCD provides medication info to the writer to program tag for medication specs (it may also include authentication); it also provides the info on the shape of the pill to the machine itself for dimensional adjustment for A, B and C in the FIGS. 5 and 6 or the database of the pills is stored at the machine memory and extracted from the information on the given pill specs. The machine loads pills into segments of the cartridge according to one pill per segment; then filled by pills cartridge with the tag programmed by the application (mHealth App) of the SCD with medication information of the pills to complete loading and tagging the cartridge. It then is transported from the loading cartridge location and another empty cartridge with blank tag is placed in the loading cartridge location of the machine.

FIG. 7 shows top view of the cartridge medication cabinet 400 in storage format, i.e. passive form abbreviated as CMC-P. It consists of the base member 430 and storage member 420 where prefilled and tagged cartridges are stored within the notches 440, 440', etc., as for instance, the cartridge 410. The CMC-P 400 is shown with the cover 460 open to expose the storage compartment 450 in the storage member 420. There are also indicator lights 495, etc., LEDs for instance, on the face of the storage member each next to location of the cartridge placement. In this particular case, the CMC-P 400 can store up to 20 prefilled and tagged cartridges with 20 indicator lights but the number might vary. The CMC-P 400 is NFC-enable device with NFC chip 480 is to read out a tag at the cartridge for the cartridge identification per the medical specs and corresponding cartridge location. The NFC chip can slide along the railing 490 to read out all tags of the cartridges stored in CMC-P 400 and to store each cartridge location and, as a result, monitor a cartridge removal and replacement. A CMC-P may also include other more long distance wireless communication (Bluetooth or WiFi, for instance) to inform a central control unit on the conditions and status of medication and cartridges at the SMC-P unit which might be useful in organizational setting such as health or patient care facility. It is also shown an opposite NFC chip position 480' closest to the bracket 520 used for installation the optional secondary dispensing module that converts CMC-P into active cartridge medication cabinet LMC-A for medication secondary dispensing to be described below.

FIG. 8 shows a side view of the CMC-P 400 with open cover 460 to show a position of one of the cartridges 410 stored in the storage compartment. The storage member 420 is placed over the base member 430. There are notches, 440, etc. for a cartridge placement. The FIG. 8 shows NFC chip 480 sliding along the railing 490 to read out all tags of the cartridges stored. There is also bracket 520 for a secondary dispensing module installation. The storage member 420 may include pressure switches 470', etc. at the bottom or/and photocell 470" to detect a cartridge placement into the storage member 420 or removal a cartridge from a given location, i.e. the device processor establishes the location number for each placed cartridge and the chip 480 authenticate it by tag's medication specs. The motor 500 performs NFC chip 480 sliding for the tag data to be processed and monitored by electronic processing unit 510.

FIG. 9 demonstrates top view of CMC-P 400' similar to one on FIG. 7 but with the full load of cartridges, 410, 410', 410", etc. The NFC chip 480" is shown at the position about closest to the bracket 520'. This is so called "home" position of the NFC chip in a CMC-P or CMC-A device. A single control device (SCD) 540 communicates with CMC-P 400" by being placed at the allocated position within its NFC working distance to the NFC chip 480' and to initiate communication between both devices. NFC-enabled smart phone may serve as the SCD.

Thus, by placing the SCD over the CMC-P, the application (mHealth App) on SCD receives the data on all stored cartridges with their locations for a cartridge monitoring for available medication, the expiration date issues, quantities, etc. The application also monitors the cartridges for a comparison with last reading for unusual removal or replacement to flag unauthorized activities. The application guides which cartridge is to be used for a given patient and records a cartridge transfer to the cartridge based pill dispenser or personal dispenser from a given CMC-P unit. Every time a cartridge is removed or placed into the CMC-P unit, its NFC chip slides over the cartridge to record and log any changes in cartridge positions with the corresponding medications.

FIG. 10 demonstrates a side view of the same device 400' from the FIG. 9. The cover 460' is open to expose the cartridges 410' to 410 in the storage member 420'. The SCD 540 is conveniently placed over the device 400' for communication between SCD and CMC-P. There is also bracket 520' for the secondary dispensing module (SDM) placement.

FIG. 11 demonstrates top view of a secondary dispensing module (SDM) 600. It includes body 610 with the bracket 640 for sliding into the bracket 520 of the FIG. 8 shown at a passive cartridge medication storage (CMC-P) device thus converting it into an active cartridge medication storage (CMC-A) device that allows for secondary medication dispensing. The body 610 incorporates motor 620 connected to the rotating shaft 260' and electronic processing unit 630. The SDM 600 includes cord 650 for connection to the attached to it the CMC-P device. The cord connection allows drawing power from the CMC-P and data exchange between the CMC-P and SDM 600. It is possible to have a direct USB or like connection between a CMC-P and SDM upon placement the SDM at the bracket of the CMC-P for power and data exchange instead of the cord 650.

FIG. 12 demonstrates a side view of the SDM 600 shown on the FIG. 11. It shows the body 610, rotating shaft 260', bracket 640 for placement over the CMC-P and cord 650.

FIG. 13 demonstrates a front view of the SDM 600 shown on the FIG. 11. It shows the body 610, rotating shaft 260' and cord 650.

FIG. 14 demonstrates a front view of one of the cartridges 410" stored in the CMC-P 400' shown on the FIG. 9. The prefilled cartridge 410" is loaded with pills, 255, etc. within with segments (compartments) of the receptacle 240'. The receptacle 240' includes ratchet 265 for the receptacle 240' rotation in steps corresponding to a number of segments of the receptacle 240'. The programmed for the medication specs tag 270" is preferably located at the opposite side over the ratchet 265 from the cartridge opening 220' through which a pill is dispensed from the cartridge.

FIG. 15 demonstrates passive cartridge medication cabinet (CMC-P) from the FIG. 9 with the attached secondary dispensing module (SDM) from the FIG. 11 to form active cartridge medication cabinet (CMC-A) 700.

The storage member 420' stores a number of cartridge numbered from cartridge 410' to cartridge 410 in the storage space 450'. The CMC-A 700 is shown with SCD 540, for instance, NFC-enabled smart phone placed over the "home" location of the NFC chip 480" for the initiation and data exchange between devices. The body 610 of the SDM is attached to the storage member 420' with its cord 650 connected to the storage member 420' power source and data processing electronics. The cartridge 410" is removed from the storage compartment 450' and placed onto the rotating shaft 260' with its cartridge opening facing the patient cup 720 placed on the allocated in base 430' imprint 710. The tag 270' of the cartridge 410" is at the top position within the working distance to the SCD 540 to enable it to read tag 270' of the cartridge 410".

The application (mHealth App) at SCD 540 communicates with CMC-A (similar to CMC-P) to light a LED 495' associated with the location of the required cartridge 410" in the storage space 450' to guide which cartridge to remove, i.e. green light for instance and then the location from which the cartridge was removed, i.e. red light for instance, to guide where a given cartridge shall be placed. The corresponding location numbers stored at the CMC-A 700 electronic processing unit are transferred between CMC-A 700 and SCD 540 to allow the application (mHealth App) to guide and monitor all events. In addition, the chip 480" reader may slides over the railing 490' to confirm the cartridge absence from the assigned location (as well as placement or replacement) and if the required cartridge is placed over the shaft 260' for pill secondary dispensing from it. The chip 480" then checks if the cartridge is placed back in the assigned place after the pill secondary dispensing into the patient cup 720. All this info is communicated to SCD 540 for resident application (mHealth App) to guide, monitor and log all steps of a cartridge handling for secondary dispensing and the corresponding status can be displayed on SCD 540 screen.

FIG. 16 demonstrated a side view of the CMC-A 700 with the cover 460' open for a cartridge access. A patient cup 720 is placed at the base 430' imprint 710. The patient cup 720 includes tag 730 programmed with patient ID also to be verified by the application (mHealth App) on the SCD 540 directly if the working distance allows or indirectly via the CDC-A 700. The body 610 of the SDM is attached to the storage member 420 together with the cord 650 to power and data transfer between electronic processing units of the SDM and the original CMC-P unit.

The method of secondary dispensing with the help of CMC-A 700 involves the following steps: the SCD 540 is placed over the CMC-A 700 to read the info on the available medication, cartridge locations, a number of times each cartridge was used, i.e. available number of pills at each cartridge, a number of pill dispensing steps from used cartridges that all correlate with the prescription regiment of the given patient per the patient ID at the cup 720 as the patient cup 720. A patient cup is part of a more general term "carrier" as any unit where the pills are deposited to from a cartridge for consecutive dispensing to a patient may take a different form. Then, the application (mHealth App) guides, monitors and controls the process of transferring correct pills from the cartridges into the carrier. The application (mHealth App) notifies on a mismatch or match between the patient regimen per the patient ID and available in CMC-A medications. The patient cup 720 placed over imprint 710 has to match with the Patient ID of the prescription; the application (mHealth App) of the SCD 540 data lights up the indicator lights of CMC-A 700 to indicate which cartridge is to be used for the required prescription regimen; one of the required cartridges, say cartridge 410", is removed and placed onto the rotating shaft 260' and SCD 340 reads the cartridge tag 270' to confirm if the cartridge removed from the CMC-A 700 is used for dispensing corresponds to the removed cartridge; the pressure switch 475' and/or photocell 475" indicate the CMC-A processor the location where the cartridge was removed for verification by the application (mHealth App); the application (mHealth App) via SCD communicates to the processors of CMC-A to activate the motor in the Secondary Dispensing Module (SDM) to rotate the receptacle of the cartridge 410" by a number segments to dispense required number pills; the cartridge 410" is placed back into the storage member 420 which is recorded by pressure switch 475' and/or photocell 475" and verified by sliding the NFC ship reader of the CMC-A unit is moved over to read the cartridge tags for communication with application (mHealth App); the process is repeated with another cartridge filled with the medication required by the patient's prescription.

In case if several pills of the same medication are required, the options are (a) to have several cartridges of the same medication to be available at the CMC-A unit or (b) the indicator light turns back to green at the used cartridge location after the corresponding cartridge is placed back from the prior use for the pill dispensing in order to guide to use it again for the second time.

The option may be to include pressure switch and/or photocell at the imprint 710 to monitor a potential removal/replacement of the patient cup 720 during secondary dispensing process while not all cartridges are yet processed per the patient's prescription. The operation may stop and the patient cup interruption is recorded on the application (mHealth App) of the SCD. In this case, the first step of the secondary dispensing method would be to place the patient cup onto the imprint at the base of CMC-A to read out the patient ID off the tag by the SCD and then to have the SCD to initiate communication with CMC-A for medication availability information. If a medication is not available, the application (mHealth App) indicates which medication is not available and which cartridge may be replaced for the cartridge with needed medication. Another option would be to use a different CMC-A. AS all loading events have been recorded, another CMC-A device is used form the point where the pill transporting to the carrier was interacted.

The modular structure of the CMC-A as a combination of CMC-P and SDM has advantage because a number of CMC-P units to store medications for patients might be significant and easily modified between CMC-P and CMC-A is a cost effective option. In addition, in case of a failure of one of the modules, there is an option to use the other one.

One embodiment of an advantage is of the secondary dispensing with CMC-A under full guidance, control and monitoring by the method described above is that all variable data and the program to control a secondary dispensing reside at the SCD only a CMC-A is fully driven by the application (mHealth App) on the SCD. The cloud based architecture of the application (mHealth App) would allow also remote management advantages to maintain and support the application. Any change in a program or data of the patients would require only update of the application (mHealth App) on SCD and keeping all dispensing device unchanged. It allows for a cost effective medication dispensing for full medication adherence.

Although several embodiments have been described in detail for purposes of illustration, various modifications may be made to each without departing from the scope and spirit of the invention. Accordingly, the invention is not to be limited, except as by the appended claims.

What is claimed is:

1. A pill dispensing system, comprising:
   a) an electronic mobile communication device having one or more non-transitory computer-readable media having computer executable code stored thereon, where the electronic mobile device comprises a wireless transmitter and receiver;
   b) a pill cartridge comprising a cartridge body having a cartridge opening, the pill cartridge having a receptacle with a plurality of segments storing a plurality of pills, where each segment is configured to be aligned with the cartridge opening allowing at least one of the plurality of pills to pass through the cartridge opening, where the cartridge body comprises a passive electronic tag storing data about the pills, and where the cartridge body stores the supply of pills separately from a pill cartridge dispenser; and
   c) the pill cartridge dispenser configured to receive at least one of the pill cartridge and configured to electromechanically control dispensing of the plurality of pills from the cartridge body, where the pill cartridge dispenser is configured to be in wireless communication with the electronic mobile communication device including receiving a first wireless signal from the electronic mobile communication device to dispense the pill from the pill cartridge and then the pill cartridge dispenser sending a second wireless signal to the electronic mobile communication device to confirm the pill dispensing event;
   wherein the electronic mobile communication device is configured to wirelessly read the data stored on the passive electronic tag of the pill cartridge or wherein the pill cartridge dispenser is configured to wirelessly read the data stored on the passive electronic tag of the pill cartridge;
   a wearable passive electronic tag having patient specific medical information, wherein the wearable passive electronic tag is configured to be worn or carried by a patient and is configured to be readable by the electronic mobile communication device;
   wherein the computer executable code comprises a routine executable by the electronic mobile communication device to wirelessly communicate with the wearable passive electronic tag to read the data.

2. The system of claim 1, wherein the computer executable code comprises a routine executable by the electronic mobile communication device to wirelessly communicate with the passive electronic tag to read the data.

3. The system of claim 2, wherein the computer executable code comprises a routine executable by the electronic mobile communication device to receive a patient dispensing schedule.

4. The system of claim 3, wherein the computer executable code comprises a routine executable by the electronic mobile communication device to process the data from the passive electronic tag with the patient dispensing schedule.

5. The system of claim 4, wherein the computer executable code comprises a routine executable by the electronic mobile communication device to determine when a medication dispensing is needed according to the patient dispensing schedule and data from the passive electronic tag.

6. The system of claim 5, wherein the computer executable code comprises a routine executable by the electronic mobile communication device to register the dispensing of the at least one pill.

7. The system of claim 1, wherein the pill cartridge dispenser is configured to receive a plurality of the pill cartridges.

8. The system of claim 1, including a loading and tagging machine configured to transform the cartridge body, the plurality of pills and a blank electronic tag into a single assembly comprising the pill cartridge, the plurality of pills and the passive electronic tag storing data thereby forming the pill cartridge.

9. The system of claim 1, wherein the wireless communication between the electronic mobile communication device and the passive electronic tag or the pill cartridge dispenser comprises short-range wireless technology or near field communication technology.

10. The system of claim 1, wherein the pill cartridge dispenser is selected from the group consisting of a personal pill dispenser, an active cartridge medication cabinet, a passive cartridge medication cabinet and a passive cartridge medication cabinet with a secondary dispensing module.

11. The system of claim 1, wherein the electronic mobile communication device is selected from the group consisting of a smart phone, an electronic tablet, an electronic wrist watch and a wearable electronic device.

12. The system of claim 1, wherein the electronic mobile communication device is configured to communicate with a centralized database over a wireless intranet or internet.

13. The system of claim 1, including an automated pharmacy machine configured to dispense a pill cartridge to an individual, the individual comprising a courier, a caretaker or a patient, where the automated pharmacy machine is configured to communicate with the electronic mobile communication device.

14. The system of claim 1, wherein the computer executable code comprises a routine executable by the electronic mobile communication device to receive a patient dispensing schedule from the wearable passive electronic tag.

15. The system of claim 14, wherein the computer executable code comprises a routine executable by the electronic mobile communication device to process the data from the wearable passive electronic tag with the patient dispensing schedule.

16. The system of claim 15, wherein the computer executable code comprises a routine executable by the electronic mobile communication device to determine when a medication dispensing is needed according to the patient dispensing schedule and data from the wearable passive electronic tag.

17. The system of claim 16, wherein the computer executable code comprises a routine executable by the electronic mobile communication device to register the dispensing of the at least one pill.

* * * * *